United States Patent [19]
Yen et al.

[11] Patent Number: 5,773,608
[45] Date of Patent: Jun. 30, 1998

[54] PROCESS FOR PREPARING STABILIZED CHITIN DERIVATIVE COMPOUNDS

[75] Inventors: Shasy-Fong Yen, Atlanta; Mary Sou, Alpharetta, both of Ga.

[73] Assignee: CIBA Vision Corporation, Duluth, Ga.

[21] Appl. No.: 675,748

[22] Filed: Jul. 3, 1996

Related U.S. Application Data

[63] Continuation-in-part of Ser. No. 516,420, Aug. 17, 1995.
[51] Int. Cl.$^6$ .................... C08B 37/08; A61K 31/73
[52] U.S. Cl. .............. 536/124; 536/20; 536/123.1; 536/127; 514/55
[58] Field of Search .................. 536/20, 123.1, 536/124, 127; 514/55

[56] References Cited

U.S. PATENT DOCUMENTS

| | | | |
|---|---|---|---|
| 4,386,151 | 5/1983 | Berger et al. | 430/228 |
| 4,946,870 | 8/1990 | Partain et al. | 514/777 |
| 5,212,162 | 5/1993 | Missel et al. | 514/54 |
| 5,318,780 | 6/1994 | Vlegas et al. | 424/427 |
| 5,362,717 | 11/1994 | Dinglian | 514/55 |
| 5,382,286 | 1/1995 | Fanning et al. | 106/162 |
| 5,420,197 | 5/1995 | Lorenz et al. | 525/54.3 |
| 5,422,116 | 6/1995 | Yen et al. | 424/427 |
| 5,550,187 | 8/1996 | Rhee et al. | 525/54.1 |

FOREIGN PATENT DOCUMENTS

| | | |
|---|---|---|
| 0356060A2 | 8/1989 | European Pat. Off. . |
| 0426368A2 | 10/1990 | European Pat. Off. . |
| 0665022A1 | 1/1994 | European Pat. Off. . |
| 01809342 | 11/1995 | European Pat. Off. . |
| 2179043 | 2/1987 | United Kingdom . |
| WO9407999 | 4/1994 | WIPO . |

OTHER PUBLICATIONS

Rao et al. *Journal of Biomaterials Applications* Oct. 1995, 10(2), 136–143.

"The Merck Index" Ninth Edition. M. Windholz et al., editors. Merck & Co., Inc., Rahway, NJ, 1976. Monograph 5575, p. 745, and monograph 8497, pp. 1126–1127. Month not available.

Drug Development and Industrial Pharmacy, pp. 2475–2489 (1989), Muco–Adhesive Liquid Ophthalmic Vehicles–Evaluation of Marcomolecular Ionic Complexes of Pilocarpine, M. F. Saettone, D., Monti, MT., Torracca, P. Chetoni, B. Giannaccini. Months not available.

Biomedical Applications of High–Purity Chitosan, PaulA. Sandford, Arild Steinnes, American Chemical Society, Chapter 28, 1991. Months not available.

Some Aspects of Chitsan Hydrogel Ointment Base Formulation, Jan Knapczyk and Robert Wyska, 6th International Conference on Chitin and Chitosan, p. 44, 1994. Months not available.

Radiation–Induced Degradation of Chitosan, P. Ulanski and J. M. Rosiak, 6th International Conference on Chitin and Chitosan, p. 54, 1994.

Chitin and Chitosan, Gudmund, Skjåk–Bræk, Thorleif Anthonsen, Paul Sandford, Elsevier Applied Science, pp. 671–677, 1990.

Review of Excipients and pHs for Parenteral Products Used in the United States, Journal of the Parenteral Drug Association, Y. J. Wang, et al., vol. 43, No. 6, pp. 452–462, 1980.

*Primary Examiner*—Kathleen K. Fonda
*Attorney, Agent, or Firm*—Michael U. Lee; R. Scott Meece

[57] ABSTRACT

A process for sterilizing a polysaccharide composition containing chitosan, a chitosan derivative or a chitin derivative without substantially degrading the polysaccharide. The process has the steps of blending the polysaccharide in a solvent to form a solution or suspension; sterilizing the solution or suspension; dissolving suspended particles, if present; and then aseptically adjusting the pH of the sterilized solution. There is additionally provided a polyol stabilizing agent suitable for the polysaccharide composition.

15 Claims, No Drawings

PROCESS FOR PREPARING STABILIZED CHITIN DERIVATIVE COMPOUNDS

CROSS REFERENCE TO RELATED APPLICATION

This is a continuation-in-part of copending U.S. application Ser. No. 08/516,420 filed Aug. 17, 1995.

BACKGROUND OF THE INVENTION

The present invention is directed to a process for sterilizing a chitin derivative composition and to a stabilized chitin derivative composition. More particularly, the present invention is directed to a process for sterilizing a chitin derivative composition while minimizing viscosity degradation of the composition and also directed to a stabilized chitin derivative composition produced by the process.

Chitin is an unbranched linear polysaccharide of N-acetyl-D-glucosamine units linked by β-1,4 bonds. The exoskeletons of insects and crustacea, e.g., crabs, lobsters and shrimps, contain large amounts of chitin, making this polysaccharide nature's second most plentiful biopolymer next to cellulose. However, chitin is not readily processible or usable since it is inert to many common aqueous and organic solvents. Attempts have been made to provide processible derivatives of chitin, and processible derivatives of chitin such as chitosan and derivatives thereof are known in the art. Chitosan is partially or completely deacetylated chitin and is a polysaccharide consisting basically of monomeric β(1-4)-D-glucosamine (A) units and monomeric β(1-4)-N-acetyl-D-glucosamine (B) units which are scattered randomly in the molecule of the polymer, wherein the polysaccharide contains at least about 60% of A and up to about 40% of B. Chitosan can be derivatized, e.g., carboxymethylated, to provide additional and/or different functional properties. Chitosan and derivatives thereof are typically soluble in acids, including mild acids, e.g., formic, acetic and propionic acids, and depending on the types of modification, certain chitosan derivatives, e.g., 0-carboxymethyl chitosan, are soluble even in water.

Chitosan has been used in medicament delivery systems. For example, U.S. Pat. No. 4,946,870 to Partain, III, et al. discloses a delivery system containing at least one aminopolysaccharide derivative for the delivery of pharmaceutical agents to a mucous membrane. U.S. Pat. No. 5,318,780 to Viegas et al. teaches a polysaccharide-containing ophthalmic drug delivery composition, and the polysaccharide of the composition can be chitosan. U.S. Pat. No. 5,422,116 to Yen et al. teaches a slow release ophthalmic drug composition that contains chitosan.

Typically, pharmaceutical compositions containing chitosan are sterilized before the compositions are packaged. Although various sterilization methods can be used to sterilize pharmaceutical compositions, high pressure steam (autoclave) sterilizing processes are typically used. In general, a conventional autoclave sterilizing process is conducted by dissolving chitosan in an acid to form a solution, and then heat-treating the solution to produce a sterilized chitosan solution. However, subjecting a chitosan-containing composition to an autoclave process tends to degrade the polysaccharide in the composition and results in a significant viscosity loss. There have been attempts to accommodate such viscosity loss. For example, a composition containing a higher concentration of the polysaccharide than desired can be prepared in anticipation of the viscosity loss during the sterilization process. Although the resulting sterilized composition produced in this fashion may have the targeted viscosity, the high concentration of polysaccharide increases the cost of the composition and may create undesirable side effects. For example, an ophthalmic pharmaceutical composition prepared in this manner may cause discomfort and/or irritation in the eye due to the high concentration of the polysaccharide.

Additionally, it is known in the art that the viscosity of a solution or gel composition containing chitosan changes over time due to gradual degradation of the chitosan. Consequently, such compositions have less than desirable stability and shelf-life.

There remains a need for a sterilizing process that does not cause significant degradation of chitosan. Additionally, there remains a need for a stabilizing agent that prolongs the shelf-life of a chitosan solution or gel composition.

SUMMARY OF THE INVENTION

In accordance with the present invention, there is provided a process for preparing a sterilized polysaccharide composition that contains a water-insoluble polysaccharide selected from chitosan, chitosan derivatives and mixtures thereof. The process has the steps of forming a suspension of chitosan in a solvent; sterilizing the suspension, thereby forming a sterilized suspension; and thereafter aseptically solubilizing the chitosan, thereby forming a sterilized polysaccharide solution. The invention additionally provides a process for sterilizing a composition containing a water-soluble chitosan or chitin derivative. The process has the steps of forming a solution of a water-soluble chitosan or chitin derivative in a solvent; adding a base to the solution, thereby forming a basic solution; sterilizing the basic solution, thereby forming a sterilized polysaccharide solution; and titrating the sterilized polysaccharide solution with an aseptic acid to a desired pH level. Unlike conventional polysaccharide sterilization processes, the present sterilization processes do not unduly deteriorate the viscosity of the polysaccharide-containing compositions.

There is additionally provided a stabilizing agent for a polysaccharide composition having a polysaccharide selected from the group consisting of chitosan, chitosan derivatives and mixtures thereof. The stabilizing agent includes a polyol having a 1, 2-diol hydrocarbon moiety. There is also provided a process for stabilizing a polysaccharide composition containing a polysaccharide selected from the group consisting of chitosan, chitosan derivatives, chitin derivatives and mixtures thereof. The process has the step of adding a polyol having a 1, 2-diol hydrocarbon moiety in the polysaccharide composition.

The sterilized stable chitosan composition is particularly useful as an excipient. For example, the chitosan composition can be used as a base or carrier material for pharmaceutical formulations, ophthalmic formulations, cosmetic formulations, dermatological protectant formulations and the like.

DETAILED DESCRIPTION OF THE INVENTION

The present invention provides a process for sterilizing a solution or gel composition containing chitosan. The present sterilization process prevents significant degradation of the polysaccharide during the sterilizing process, compared to conventional autoclave sterilization processes. The term chitosan as used herein indicates chitosan, a chitosan derivative or a mixture thereof, unless otherwise indicated. Hereinafter, the invention is described with a solution composition for illustration purposes although the invention is useful for sterilizing chitosan compositions that have a wide range of different viscosities, including low viscosity composition, e.g., solutions, and high viscosity compositions, e.g., gels. According to the present invention, the sterilized chitosan solution composition may have a wide range of chitosan content levels and a wide range of viscosity levels. Desirably, the chitosan solution composition has between about 0.4 wt% and about 50 wt %, more desirably between about 0.45 wt % and about 20 wt %, most desirably between about 0.5 wt % and about 10 wt %, of chitosan, based on the total weight of the composition. Desirably, the chitosan composition has a viscosity between about 5 cps and about 500,000 cps, more desirably between about 100 cps and about 300,000 cps, most desirably between about 1,000 cps and about 100,000 cps, as measured using a Bohlin CS Rheometer (plate-plate geometry).

The sterilization process has the steps of blending chitosan in an aqueous solvent, e.g., water; sterilizing the chitosan solution or suspension; dissolving suspended particles, if present; and then aseptically adjusting the pH of the sterilized solution. In accordance with the present invention, when water-insoluble particulate chitosan is used, the chitosan particles are suspended to form a chitosan suspension in an aqueous solvent having a pH desirably equal to or higher than about 6, more desirably equal to or higher than about 7. The chitosan suspension is sterilized in an autoclave, and then the pH of the sterilized chitosan suspension is lowered using an aseptic acid to dissolve the suspended chitosan particles, thereby forming a sterilized chitosan solution. As indicated above, different types of chitosan derivatives dissolve at different pH levels. Accordingly, the pH of the sterilized suspension is adjusted to a suitable pH level that is sufficiently low enough to solubilize the suspended chitosan particles. However, the pH of the sterilized suspension should not be unduly lowered to a level that can promote acidic degradation of the polysaccharide. For example, when non-derivatized chitosan is used, the pH of the sterilized suspension is desirably adjusted to between about 5 and about 6.5 to form a sterilized chitosan solution. In accordance with the present invention, any aseptic acid can be used to adjust the pH of the sterilized chitosan solution. Of the suitable acids, particularly suitable acids for the invention are monovalent counter ion-containing acids, e.g., hydrochloric acid, acetic acid, formic acid, lactic acid, malic acid, malonic acid, propionic acid, pyruvic acid and succinic acid. After the chitosan particles are dissolved to form a sterilized chitosan solution, the pH of the solution can again be adjusted with an aseptic acid or base to a desired level. The term suspension as used herein indicates a mixture in which a liquid medium contains dispersed small particles that substantially are not solubilized, and the term solution indicates a uniform mixture at the molecular or ionic level of one or more solutes in a liquid solvent. The term water-insoluble chitosan as used herein indicates chitosan, e.g., typical non-derivatized chitosan, that is not significantly soluble at a pH equal to or higher than about 6, while the term water-soluble chitosan as used herein indicates a chitosan derivative that is soluble even at a pH equal to or higher than about 6. The term soluble as used herein indicates more than 0.1 g of a solute can be dissolved in 1 liter of a solvent.

As another embodiment of the present invention, when a water-soluble chitosan derivative is use, the chitosan is dissolved in an aqueous solvent to form a solution. The pH of the solution is raised with a base or an alkaline material to a basic level, desirably to a pH equal to or higher than about 8, more desirably equal to or higher than about 11. The basic chitosan solution is sterilized, forming a sterilized chitosan solution. With an aseptic acid, the pH of the sterilized solution is then adjusted to a desired level. Basic materials useful for adjusting the chitosan solution include sodium hydroxide, potassium hydroxide, magnesium hydroxide, sodium carbonate, potassium carbonate, sodium bicarbonate, potassium bicarbonate, ammonia, various amines and the like. For this embodiment of the invention, it is particularly desirable to add a stabilizing agent of the present invention in the chitosan solution before the solution is subjected to the sterilization process. Suitable stabilizing agents are further discussed below. Although this process embodiment of the invention is illustrated with water-soluble chitosan derivatives, this embodiment can also be used to sterilize compositions containing a water-soluble non-deacetylated chitin derivative.

As indicated above, suitable chitosan and derivatives thereof for the present invention include water-insoluble and water-soluble chitosan and chitosan derivatives, and water-soluble chitin derivatives. Water-insoluble chitosan suitable for the invention include non-derivatized chitosan and chitosan derivatives that, for example, contain an alkyl group which does not have a dissociable functional moiety. Exemplary water-insoluble chitosan derivatives include N-alkyl chitosan, 6-alkyloxy chitosan, N,O-alkyl chitosan, N,N-dialkyl chitosan and N-halochitosan. Of the water-insoluble chitosan and chitosan derivatives, chitosan is particularly suitable. Water-soluble chitosan derivatives suitable for the invention include chitosan polymers having one or more hydrophilic substituents at 2-N and/or 6-position of the glucosamine. Exemplary hydrophilic substituents for water-soluble chitosan derivatives include carboxyalkyl, e.g., carboxymethyl, carboxyethyl, carboxypropyl and carboxybutyl; hydroxyalkyl, e.g., hydroxyethyl, hydroxypropyl, hydropybutyl; sulfuryl; phosphoryl; amino and the like. Suitable water-soluble chitosan derivatives include O-carboxymethyl chitosan, N,O-carboxymethyl chitosan, N-carboxymethyl chitosan, N,O-sulfur chitosan, 1-deoxygalactit-1-yl-chitosan, 1-deoxygalucit-1-yl-chitosan and N,O-ethylamine chitosan. Of the water-soluble chitosan derivatives, particularly suitable are 0-carboxymethyl chitosan, N,O-carboxymethyl chitosan and N-carboxymethyl chitosan. Water-soluble non-deacetylated chitin derivatives suitable for the invention include N,O-ethylamine chitin and 0-sulfur chitin.

Chitosan suitable for the present invention can be prepared by deacetylation of chitin, e.g., as described in U.S. Pat. No. 3,953,068., and chitosan derivatives can be prepared, e.g., as described in U.S. Pat. No. 4,619,995. Chitosan, chitosan derivatives and chitin derivatives are commercially available from, e.g., Nova Chem, Limited, Canada; Protan, Incorporated, U.S.A.; Cabomer, Incorporated, U.S.A.; and Pronova Biopolymer, Limited, Norway.

In accordance with the invention, suitable aqueous solvents include water and aqueous solvents containing up to about 50% of an organic co-solvent, e.g. glycerol, ethylene glycol, polyethylene glycol, propylene glycol, polypropylene glycol, vinyl alcohol, polyvinyl alcohol, vinyl pyrolidone and polyvinyl pyrolidone.

The present invention additionally provides stabilizing agents suitable for chitosan and chitin compositions. The stabilizing agents include monomeric and oligomeric polyol compounds having a 1, 2-diol hydrocarbon moiety. The stabilizing agents may have an aromatic or aliphatic structure. Exemplary suitable stabilizing agents include alditols, e.g., mannitol and sorbitol; glycols, e.g., ethylene glycol;

and saccharide, e.g., sucrose, lactose, fructose and maltose. Of these, particularly suitable are alditols, and more particularly suitable are mannitol and sorbitol. Although the chitosan or chitin composition may contain various amounts of the stabilizing agent, the composition desirably contains between about 0.5 wt % and about 20 wt % of the stabilizing agent, more desirably between about 1.0 wt % and about 15 wt %, most desirably between about 1.5 wt % and about 12 wt %, based on the total weight of the chitosan or chitin composition. The stabilizing agent can be added before or after the chitosan or chitin composition is subjected to the sterilization process. Desirably, however, the stabilizing agent is added before the composition is autoclaved, especially when a water-soluble chitosan or chitin is utilized. It has been found that the polyol stabilizing agent significantly diminishes the thermal degradation effect of autoclaving processes. In addition, it has been found that the stabilizing agent prolongs the stability and shelf-life of the sterilized chitosan compositions by retarding gradual breakdown or degradation of the chitosan and chitin.

The polysaccharide composition of the present invention may further contain other additives suitable for polysaccharides, e.g., tonicity enhancing agents and antioxidants. For example, suitable tonicity enhancing agent include alkali metal halides, e.g., sodium or potassium chloride; mannitol; sorbitol and the like. Other suitable additives include known excipients such as various excipients disclosed by Y. J. Wang et al. in Journal of the Parenteral Drug Association, Vol. 43, No. 6, pages 452–462, 1980.

In accordance with the present invention, the sterilized polysaccharide composition may additionally contain one or more active ingredients, including pharmaceutical and ophthalmic drugs, dermatological protectants, fragrances, antioxidants and the like. Depending on the stability of the active ingredients, the ingredients can be added before or after the suspension or solution is sterilized. Suitable pharmaceutically active ingredients for the present invention include antibiotics, antiinflammatory agents, antifungal agents, antiviral agents, miotic agents and the like. Typically, a pharmaceutically or ophthalmically effective concentration of an active ingredient is added to the chitosan solution. For example, from about 0.001% to about 10% by weight, desirably from about 0.01% to about 5% by weight, of an active ingredient is blended with the chitosan solution.

The sterilized chitosan solution is particularly suitable for forming ophthalmic formulations that deliver pharmaceutically active ingredients to the ocular environment. In accordance with the present invention a wide variety of ingredients can be formulated with the chitosan solution. Suitable agents include steroidal antiinflammatory agents, e.g., prednisolone acetate, prednisolone, fluorometholone, fluorometholone acetate, hydrocortisone, hydrocortisone acetate and the like; non-steroidal antiinflammatory agents, e.g., diclofenac, flurbiprofen, suprofen, prioxicam, ketorolac and the like; antibiotics, e.g., chloramphenicol, ciprofloxacin, gentamycin, sulfacetamide, tetracycline, penicillin, neomycin, moxalactam, erythromycin, kinamycin, methicillin, ampicillin, cefazolin and the like; antifungal agents, e.g., amphotericin B, flucytosine, natamycin, myconazole and the like; miotic agents, e.g., carbachol, pilocarpine, physostigmine, demecarium, echothiophate and the like; antiglaucoma agents, e.g., dipiverfrin, epinephrine, hydralazine, pilocarpine, carbachol, betaxolol, carteolol, lerobunolol, metipranolol, timolol, isosorbide, azetazolamide and the like; ocular decongestants, e.g., naphazoline, phenylephrine, tetrahydrozoline and the like; and ocular nutrients, e.g., various forms of Vitamin A.

The sterilization process of the present invention provides a highly useful method, especially in conjunction with the polyol stabilizing agent, for producing stabilized chitosan and chitin compositions that are stable not only during the sterilization process but also over extended storage. The sterilization process is particularly suitable for preparing pharmaceutical and ophthalmological compositions.

The present invention is further illustrated with the following examples. The examples are presented for illustrative purposes and are not intended to limit the scope of the invention.

EXAMPLES

Viscosity measurements are made at 25° C. using a Bohlin CS-10 or V88 rheometer, manufactured by Bohlin.

Example 1 (Ex1)

Example 1 illustrates the invention with a water-insoluble chitosan. 4 g of chitosan, Seacure 343 obtained from Pronova Biopolymer, Norway, is dispersed in 150 ml of distilled water to form a suspension. The suspension is autoclaved at 121° C. for 15 minutes in a Yamato SM32 autoclave and cooled. Hydrochloric acid, conc., is slowly added to the sterilized suspension while being stirred to dissolve the chitosan particles. The weight of the resulting chitosan solution is brought up to 200g using sterilized distilled water, forming a sterilized 2% chitosan solution. The pH and viscosity of the sterilized solution are measured. A series of viscosity measurements are made at shear rates between 0.5/second and 1000/second, and the viscosity value at 10/second is extrapolated from the measured viscosity data. The results are shown in Table 1.

Comparative Example 1 (C1)

4 g of chitosan, Seacure 343, is dispersed in 150 ml of distilled water to form a suspension. Hydrochloric acid, conc., is slowly added while being stirred until the chitosan particles are dissolved. The weight of the resulting chitosan solution is brought up to 200g using distilled water, forming a non-sterilized 2% chitosan solution. The pH and viscosity of the sterilized solution are measured. The results are shown in Table 1.

Comparative Example 2 (C2)

4 g of chitosan, Seacure 343, is dispersed in 150 ml of distilled water to form a suspension. Hydrochloric acid, conc., is slowly added while being stirred until the chitosan particles are dissolved, forming a chitosan solution. The solution is autoclaved at 121° C. for 15 minutes in a Yamato SM32 autoclave. The sterilized solution is taken out of the autoclave, and the weight of the resulting chitosan solution is brought up to 200g using sterilized distilled water, forming a sterilized 2% chitosan solution. The pH and viscosity of the sterilized solution are measured. The results are shown in Table 1.

Example 2 (Ex2)

Example 1 was repeated except a different grade of chitosan is used, namely Seacure 243, which is available from Pronova Biopolymer, Norway.

Comparative Examples 3–4 (C3–C4)

Comparative Examples 1 and 2, respectively, are repeated except Seacure 243 chitosan is used.

TABLE 1

| Example | pH | Viscosity (pascal) @ 10/second shear rate |
|---|---|---|
| Ex1 | 1.65 | 11 |
| C1 | 1.60 | 8.8 |
| C2 | 1.57 | 0.092 |
| Ex2 | 1.65 | 1.5 |
| C3 | 1.65 | 1.1 |
| C4 | 1.63 | 0.068 |

The high viscosity data of Examples 1 and 2 compared to the low viscosity data of similarly sterilized chitosan solutions, Comparative Examples 2 and 4, clearly demonstrate that the sterilization process of the present invention prevents the thermal degradation of chitosan during an autoclave sterilization process. Given that the chitosan compositions are sterilized under virtually the same conditions and the only difference is the chitosan solubilization sequence, i.e., the chitosan of Examples 1 and 2 is solubilized after having been sterilized whereas the chitosan of Comparative Examples 3 and 4 is solubilized before being sterilized, it is highly surprising to find that the viscosities of the chitosan compositions of Examples 1 and 2 are not unfavorably affected by the sterilization process and not much different from the viscosity data of Comparative Examples 1 and 2, which are not subjected to the sterilization process.

Although the viscosity data of Examples 1 and 2 are higher than those of the non-sterilized compositions, i.e., Comparative Examples 1 and 2, it is believed that the viscosity increase does not indicate a significant change in the chitosan structure but resulted from the solubilization of the suspended chitosan particles.

Example 3 (Ex3)

Example 3 illustrates the invention with a water-soluble chitosan derivative. 15 g of N,O-carboxyl methyl chitosan, available from Protan Laboratories, Redmond, Wash., is dissolved in 440 ml of distilled water. The pH of the chitosan solution is adjusted with a 50% sodium hydroxide solution to 12. The solution is diluted with water to obtain a 3.1% chitosan solution. The viscosity of the solution is measured. The chitosan solution is then autoclaved in a Yamato SM32 autoclave at about 121° C. for 15 minutes. The weight of the autoclaved solution is adjusted with water to accommodate the weight loss due to evaporation during the autoclaving procedure. The viscosity of the solution is measured in accordance with the procedure outlined in Example 1. The viscosity measurement at the 1/second shear rate is shown in Table 2.

Example 4 (Ex4)

Example 3 is repeated except 13.92 g of mannitol, USP grade and available from Mallinckrodt, is added to the chitosan solution and dissolved before the pH of the solution is adjusted with sodium chloride. The viscosity measurement is shown in Table 2.

Comparative Example 3 (C3)

Example 3 was repeated except the pH of the chitosan solution is adjusted to 7.5 and then autoclaved.

Comparative Example 4 (C4)

Example 4 was repeated except the pH of the chitosan solution is adjusted to 7.7 and then autoclaved.

TABLE 2

| Example | pH | Viscosity (pascal) pre-sterilization @ 1/second shear rate | Viscosity (pascal) post-sterilization @ 1/second shear rate | % Viscosity Change |
|---|---|---|---|---|
| Ex3 | 12 | 2.66 | 0.75 | 72% |
| Ex4 | 12 | 6.41 | 4.63 | 28% |
| C3 | 7.5 | 2.64 | 0.40 | 85% |
| C4 | 7.7 | 2.16 | 0.25 | 88% |

The above results illustrate that the present sterilization process, especially in conjunction with the addition of the stabilizing agent, significantly improves the sterilization stability of chitosan compositions.

Examples 5–7 (Ex5–Ex7)

A 1% chitosan solution is prepared using Secure 343 and distilled water. Into the chitosan solution, various polyol stabilizing agents, as indicated in Table 3, are added. The stabilized solutions are placed flasks and stored in an oven which is set at 55° C. The viscosity of the solutions is periodically measured with a Bohlin rheometer at a 1/125 second shear rate, and the viscosity data are normalized with respect to the initial viscosity of each solution. The results are shown in Table 3.

Comparative Example 5 (C5)

Example 5 is repeated except no stabilizing agent is added. The results are shown in Table 3.

TABLE 3

| Example | Stabilizing Agent | Stabilizing Agent Content | Time in Weeks 0 | 1 | 4 |
|---|---|---|---|---|---|
| | | | Normalized Viscosity | | |
| Ex5 | Mannitol | 3.5% | 100% | 54% | 32% |
| Ex6 | Sorbitol | 5.5% | 100% | 56% | 28% |
| Ex7 | Glycerol | 2.0% | 100% | 45% | 20% |
| C5 | — | — | 100% | 2% | 1% |

The viscosity data of Table 3 demonstrate that the polyol stabilizing agents of the present invention stabilize chitosan compositions. It is believed that the stabilizing agents inhibit the gradual breakdown of chitosan over time. For example, the chitosan composition containing the mannitol stabilizing agent retained 32% of its original viscosity in four weeks, whereas the same composition without a stabilizing agent significantly deteriorated and retained only 1% of its original viscosity.

What is claimed is:

1. A process for preparing a sterilized polysaccharide composition, said composition comprising a polysaccharide selected from the group consisting of N-alkyl chitosan, 6-O-alkyloxy chitosan, N,O-alkyl chitosan, N,N-dialkyl chitosan, N-halochitosan, O-carboxymethyl chitosan N,O-carboxymethyl chitosan, N-carboxymethyl chitosan, N,O-sulfur chitosan, 1-deoxygalactit-1-yl-chitosan, 1-deoxygalucite-1-yl-chitosan, N,O-ethylamine chitosan and mixtures thereof, which process comprises the steps of:

a) forming a suspension of said polysaccharide in a solvent, said polysaccharide being substantially insoluble in said solvent;

b) sterilizing said suspension, thereby forming a sterilized suspension; and c) thereafter, solubilizing said polysaccharide, thereby forming a sterilized polysaccharide solution.

2. The process of claim 1 wherein said solvent is water.

3. The process of claim 1 wherein said suspension is thermally sterilized.

4. The process of claim 1 wherein said sterilized suspension of said polysaccharide is solubilized by adding an aseptic acid.

5. The process of claim 1 wherein said polysaccharide is chitosan, said suspension is sterilized in an autoclave and said sterilized suspension of said polysaccharide is solubilized by adding an aseptic acid.

6. A process for preparing a sterilized polysaccharide composition, said composition comprising a water-soluble polysaccharide selected from chitosan derivatives, chitin derivatives and mixtures thereof, which process comprises the steps of:
 a) forming a solution of said polysaccharide in an aqueous solvent, said polysaccharide being substantially soluble in said solvent,
 b) changing the pH of said solution to form a basic solution,
 c) sterilizing said basic solution, thereby forming a sterilized polysaccharide solution, and
 d) titrating said sterilized polysaccharide solution with an aseptic acid to a desired pH,
 wherein said chitosan derivatives are selected from the group consisting of chitosan polymers having one or more hydrophilic substitutents at 2-N and/or 6O positions said hydrophilic substitutents being selected from the group consisting of carboxyalkyl hydroxyalkyl, sulfuryl, phosphoryl and amino, and said chitin derivatives are selected from the group consisting of N,O-ethylamine chitin and O-sulfur chitin.

7. The process of claim 6 wherein said composition further comprises a polyol having a 1, 2-diol hydrocarbon moiety.

8. The process of claim 6 wherein said solvent is water.

9. The process of claim 6 wherein said basic solution has a pH equal to or higher than about 8 and is formed by adding a base or an alkaline material.

10. The process of claim 6 wherein said solution is thermally sterilized.

11. The process of claim 7 wherein said solution is sterilized in an autoclave.

12. A process for producing a stabilized, sterilized polysaccharide solution composition comprising a polysaccharide selected from the group consisting of chitosan, chitosan derivatives, chitin derivatives and mixtures thereof, which process comprises the step of adding to said solution composition a polyol having a 1, 2-diol hydrocarbon moiety before said solution composition is subjected to a sterilizing process, wherein said sterilizing process has a degradation effect on said solution composition and said polyol diminishes said, degradation effect, wherein said chitosan derivatives are selected from the group consisting of N-alkyl chitosan, 6-O-alkyloxy chitosan, N,O-alkyl chitosan N,N-dialkyl chitosan, N-halochitosan, and chitosan polymers having one or more hydrophilic substitutents at 2-N and/or 6-O positions, said hydrophilic substitutents being selected from the group consisting of carboxyalkyl hydroxyalkyl, sulfuryl, phosphoryl and amino, and said chitin derivatives are selected from the group consisting of N,O-ethylamine chitin and O-sulfur chitin.

13. The process of claim 12 wherein said polyol is selected from the group consisting of alditols, glycols and saccharides.

14. The process of claim 13 wherein said polyol is selected from the group consisting of mannitol and sorbitol.

15. The process of claim 14 wherein said polysaccharide composition has between about 0.5 wt % and about 20 wt %, based on the total weight of the composition, of said polyol.

* * * * *